United States Patent
Delaloye

(10) Patent No.: US 12,115,070 B2
(45) Date of Patent: *Oct. 15, 2024

(54) IMPLANTABLE VALVE WITH ATTACHED POLYMERIC COMPONENTS

(71) Applicant: Symetis SA, Ecublens (CH)

(72) Inventor: Stephane Delaloye, Buelach (CH)

(73) Assignee: Symetis SA, Ecublens (CH)

( * ) Notice: Subject to any disclaimer, the term of this patent is extended or adjusted under 35 U.S.C. 154(b) by 630 days.

This patent is subject to a terminal disclaimer.

(21) Appl. No.: 17/232,313

(22) Filed: Apr. 16, 2021

(65) Prior Publication Data

US 2021/0228357 A1 Jul. 29, 2021

Related U.S. Application Data

(63) Continuation of application No. 16/293,904, filed on Mar. 6, 2019, now Pat. No. 10,980,636.

(60) Provisional application No. 62/640,240, filed on Mar. 8, 2018.

(51) Int. Cl.
*A61F 2/24* (2006.01)

(52) U.S. Cl.
CPC .......... *A61F 2/2463* (2013.01); *A61F 2/2418* (2013.01); *A61F 2/2454* (2013.01); *A61F 2/2466* (2013.01); *A61F 2/2403* (2013.01); *A61F 2220/0075* (2013.01)

(58) Field of Classification Search
CPC .... A61F 2/2463; A61F 2/2418; A61F 2/2454; A61F 2220/0075
See application file for complete search history.

(56) References Cited

U.S. PATENT DOCUMENTS

| 8,246,678 B2 | 8/2012 | Salahieh et al. |
| 8,845,720 B2 | 9/2014 | Conklin |
| 9,089,422 B2 | 7/2015 | Ryan et al. |
| 9,226,826 B2 | 1/2016 | Rust |

(Continued)

FOREIGN PATENT DOCUMENTS

| CN | 111818878 | 10/2020 |
| EP | 3761907 | 1/2021 |

(Continued)

OTHER PUBLICATIONS

"First Office Action," for Japanese Patent Application No. 2020-546959 mailed Nov. 24, 2021 (10 pages) with English Translation.

(Continued)

*Primary Examiner* — Suzette J Gherbi
(74) *Attorney, Agent, or Firm* — Pauly, DeVries Smith & Deffner LLC

(57) ABSTRACT

Embodiments include implantable valves with attached polymeric components. In an embodiment, an implantable valve is included having a frame comprising a plurality of frame struts. The frame defines a central lumen and at least one of the frame struts defines a connection aperture. The implantable valve can include at least one valve leaflet including a coaptation edge and two connection portions, with one connection portion disposed on either end of the coaptation edge. The connection portion can be disposed within the connection aperture thereby coupling the valve leaflet to the frame. Other embodiments are also included herein.

20 Claims, 8 Drawing Sheets

(56) References Cited

U.S. PATENT DOCUMENTS

| | | | |
|---|---|---|---|
| 9,333,075 B2* | 5/2016 | Biadillah | A61F 2/2418 |
| 9,744,031 B2 | 8/2017 | Girard et al. | |
| 9,848,981 B2 | 12/2017 | Suri et al. | |
| 9,895,221 B2 | 2/2018 | Vidlund | |
| 10,028,826 B2 | 7/2018 | Yohanan et al. | |
| 10,098,734 B2 | 10/2018 | Hoang | |
| 10,201,418 B2* | 2/2019 | Biadillah | A61F 2/2418 |
| 10,219,897 B2* | 3/2019 | Essinger | A61F 2/2436 |
| 10,258,464 B2* | 4/2019 | Delaloye | A61F 2/2409 |
| 10,716,662 B2* | 7/2020 | Delaloye | A61F 2/2418 |
| 10,980,636 B2* | 4/2021 | Delaloye | A61F 2/2454 |
| 11,766,331 B2* | 9/2023 | Vismara | A61F 2/2487 600/16 |
| 2014/0018915 A1 | 1/2014 | Biadillah et al. | |
| 2015/0265402 A1* | 9/2015 | Centola | A61F 2/2418 623/2.18 |
| 2015/0320556 A1 | 11/2015 | Levi et al. | |
| 2016/0074162 A1* | 3/2016 | Braido | A61F 2/2433 623/2.38 |
| 2016/0106537 A1 | 4/2016 | Christianson et al. | |
| 2016/0158007 A1* | 6/2016 | Centola | A61F 2/2418 623/2.11 |
| 2016/0199183 A1* | 7/2016 | Braido | A61F 2/2418 623/2.18 |
| 2016/0331528 A1* | 11/2016 | Parker | D01D 5/18 |
| 2017/0181854 A1* | 6/2017 | Christianson | A61F 2/2412 |
| 2017/0196687 A1* | 7/2017 | Braido | A61F 2/243 |
| 2017/0231760 A1* | 8/2017 | Lane | A61F 2/2436 623/2.11 |
| 2017/0348100 A1 | 12/2017 | Lane et al. | |
| 2018/0021127 A1* | 1/2018 | Yohanan | A61F 2/2412 623/1.13 |
| 2018/0271650 A1* | 9/2018 | Delaloye | A61F 2/243 |
| 2018/0318074 A1 | 11/2018 | Yohanan et al. | |
| 2019/0201193 A1* | 7/2019 | Delaloye | A61F 2/2412 |
| 2019/0274832 A1 | 9/2019 | Delaloye | |
| 2019/0314151 A1* | 10/2019 | Biadillah | A61F 2/2418 |
| 2021/0205076 A1* | 7/2021 | Parker | D01D 7/00 |

FOREIGN PATENT DOCUMENTS

| | | |
|---|---|---|
| WO | 2012032187 | 3/2012 |
| WO | 2016164209 | 10/2016 |
| WO | 2017103830 | 6/2017 |
| WO | 2017190161 | 11/2017 |
| WO | 2019170698 | 9/2019 |

OTHER PUBLICATIONS

"First Office Action," for Chinese Patent Application No. 201980017708.9 mailed Feb. 22, 2023 (13 pages) with English summary.

Falk, Volkmar "TAVI: Future Developments," Powerpoint presentation from the 4th Aortic Live Symposium Oct. 23-24, 2017 in Hamburg, Germany (74 pages).

File History for U.S. Appl. No. 16/293,904 downloaded Jun. 3, 2021 (127 pages).

"International Preliminary Report on Patentability," for PCT Application No. PCT/EP2019/055491 mailed Sep. 17, 2020 (11 pages).

"Invitation to Pay Additional Fees," for PCT Application No. PCT/EP2019/055491 mailed Jun. 13, 2019 (13 pages).

"Response to Communication Pursuant to Rules 161(1) and 162 EPC," for European Patent Application No. 19710628.9 filed Apr. 22, 2021 (10 pages).

Walther, "ACURATE neo Aortic Bioprosthesis for IMplantation using the ACURATE neo TA Transapical Delivery System in Patiends with Severe Aortic Stenosis," Clinical Investigation Plan by Symetis S.A., Sep. 8, 2015 retrieved from URL <https://clinicaltrials.gov/ProvidedDocs/28/NCT02950428/Prot_000.pdf> on Mar. 26, 2019 (76 pages).

"Second Office Action," for Chinese Patent Application No. 201980017708.9 mailed Oct. 27, 2023 (11 pages) with English Summary.

* cited by examiner

IMPLANTABLE VALVE WITH ATTACHED POLYMERIC COMPONENTS

This application is a continuation application of U.S. patent application Ser. No. 16/293,904, filed Mar. 6, 2019, which claims the benefit of U.S. Provisional Application No. 62/640,240, filed Mar. 8, 2018, the contents of which are herein incorporated by reference in their entireties.

FIELD OF THE TECHNOLOGY

The present application relates to an implantable valve. More specifically, the present application relates to the connection of polymeric valve components to the valve frame.

BACKGROUND

Heart function can be significantly impaired when a heart valve is not functioning properly. Potential causes for heart valve malfunction include dilation of an annulus around the valve, ventricular dilation, and a prolapsed or misshapen valve leaflet. When the heart valve is unable to close properly, the blood within a heart chamber can regurgitate, or leak backwards through the valve.

Valve regurgitation may be treated by replacing or repairing a diseased valve, such as an aortic valve. Surgical valve replacement is one method for treating the diseased valve. Minimally invasive methods of treatment, such as transcatheter aortic valve replacement (TAVR), generally involve the use of delivery catheters that are delivered through arterial passageways or other anatomical routes into the heart to replace the diseased valve with an implantable prosthetic heart valve. Leaflets of such valves have been formed from various materials including synthetic materials and animal tissues. Leaflets have been positioned within a frame to maintain or limit the blood flow through a prosthetic valve. Attaching the leaflets and other non-frame components of the valve to the frame is normally accomplished via sutures.

SUMMARY

In a first aspect, an implantable valve is included. The implantable valve can include a frame, and at least one valve leaflet. The frame can include a plurality of frame struts. The frame can define a central lumen. At least one of the frame struts can define a connection aperture. The valve leaflet can include a coaptation edge and two connection portions. One connection portion can be disposed on either end of the coaptation edge. The connection portion can be disposed within the connection aperture thereby coupling the valve leaflet to the frame.

In a second aspect, in addition to one or more of the preceding or following aspects, or in the alternative to some aspects, the connection aperture can extend at least 80 percent through the strut.

In a third aspect, in addition to one or more of the preceding or following aspects, or in the alternative to some aspects, the connection aperture can extend completely through the strut.

In a fourth aspect, in addition to one or more of the preceding or following aspects, or in the alternative to some aspects, the connection portion of the valve leaflet can extend through the connection aperture.

In a fifth aspect, in addition to one or more of the preceding or following aspects, or in the alternative to some aspects, the connection portion can encircle a portion of the strut.

In a sixth aspect, in addition to one or more of the preceding or following aspects, or in the alternative to some aspects, the connection portion can both encircle a portion of the strut and extend through a connection aperture in that same portion of the strut.

In a seventh aspect, in addition to one or more of the preceding or following aspects, or in the alternative to some aspects, the implantable valve can further include a plurality of struts, each of the struts can define a plurality of connection apertures.

In an eighth aspect, in addition to one or more of the preceding or following aspects, or in the alternative to some aspects, the density of connection apertures can vary along the length of a strut.

In a ninth aspect, in addition to one or more of the preceding or following aspects, or in the alternative to some aspects, the density of connection apertures can be the highest at a portion of the frame where the at least one leaflet is subjected to the highest concentration of stresses adjacent to the frame.

In a tenth aspect, in addition to one or more of the preceding or following aspects, or in the alternative to some aspects, the plurality of frame struts can define a lower crown, an upper crown and a plurality of stabilization arches.

In an eleventh aspect, in addition to one or more of the preceding or following aspects, or in the alternative to some aspects, the at least one leaflet can be formed of a thermoplastic polymer.

In a twelfth aspect, in addition to one or more of the preceding or following aspects, or in the alternative to some aspects, the connection aperture can have a diameter of at least 0.1 mm and not more than 0.4 mm.

In a thirteenth aspect, in addition to one or more of the preceding or following aspects, or in the alternative to some aspects, the implantable valve can further include an inner skirt. The inner skirt can be disposed on a luminal surface of the frame. The inner skirt can include a connection projection that extends into a connection aperture defined by a strut thereby coupling the inner skirt to the frame.

In a fourteenth aspect, in addition to one or more of the preceding or following aspects, or in the alternative to some aspects, the inner skirt can be formed of a thermoplastic polymer.

In a fifteenth aspect, in addition to one or more of the preceding or following aspects, or in the alternative to some aspects, the inner skirt can be formed of the same thermoplastic polymer as the at least one valve leaflet.

In a sixteenth aspect, in addition to one or more of the preceding or following aspects, or in the alternative to some aspects, the implantable valve can include an outer skirt. The outer skirt can be disposed on an abluminal surface of the frame. The outer skirt can include a connection projection that extends into a connection aperture defined by a strut thereby coupling the outer skirt to the frame.

In a seventeenth aspect, in addition to one or more of the preceding or following aspects, or in the alternative to some aspects, an implantable valve is included. The implantable valve can include a frame and an inner skirt. The frame can include a plurality of frame struts. The frame can define a central lumen. At least one of the frame struts can define a connection aperture. The inner skirt can be disposed on a luminal surface of the frame. The inner skirt can include a connection projection that extends into a connection aperture defined by a strut thereby coupling the inner skirt to the frame.

In an eighteenth aspect, in addition to one or more of the preceding or following aspects, or in the alternative to some aspects, the inner skirt can be formed of a thermoplastic polymer.

In a nineteenth aspect, in addition to one or more of the preceding or following aspects, or in the alternative to some aspects, an implantable valve is included. The implantable valve can include a frame and an outer skirt. The frame can include a plurality of frame struts. The frame can define a central lumen. At least one of the frame struts can define a connection aperture. The outer skirt can be disposed on an abluminal surface of the frame. The outer skirt can include a connection projection that extends into a connection aperture defined by a strut thereby coupling the outer skirt to the frame.

In a twentieth aspect, in addition to one or more of the preceding or following aspects, or in the alternative to some aspects, the outer skirt can be formed of a thermoplastic polymer.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present application is defined by the appended claims and their legal equivalents.

BRIEF DESCRIPTION OF THE FIGURES

The technology may be more completely understood in connection with the following drawings, in which.

While the technology is susceptible to various modifications and alternative forms, specifics thereof have been shown by way of example and drawings, and will be described in detail. It should be understood, however, that the application is not limited to the particular embodiments described. On the contrary, the application is to cover modifications, equivalents, and alternatives falling within the spirit and scope of the technology.

DETAILED DESCRIPTION

The human body has four heart valves: a pulmonary valve, a tricuspid valve, an aortic valve and a mitral valve. The purpose of the heart valves is to allow blood to flow in a particular direction through the heart and from the heart into the major blood vessels connected to the heart, such as the aorta and pulmonary artery. As the heart muscle contracts and relaxes, the valves open and shut, letting blood flow into the ventricles and atria at alternate times.

Prosthetic valves designed to replace a valve in a human body frequently include two or more leaflets (commonly three) that are attached to a frame. Prosthetic valves can be configured to allow one-way flow through the valve, such as by separating the leaflets from each other to open the valve thereby allowing flow and joining together (valve leaflet coaptation) to close the valve thereby blocking flow. In some cases, prosthetic valves can further include an inner skirt and/or an outer skirt to restrict the path of flow through the valve.

Various embodiments of attaching polymeric components, such as the leaflets, the inner skirt, and the outer skirt to the frame are disclosed herein. In some embodiments, the polymeric components can be attached or coupled to the frame through a polymeric over molding process. In some embodiments, the polymeric component can be attached to the frame via increased surface area and/or a form fitting configuration.

Figure 1:
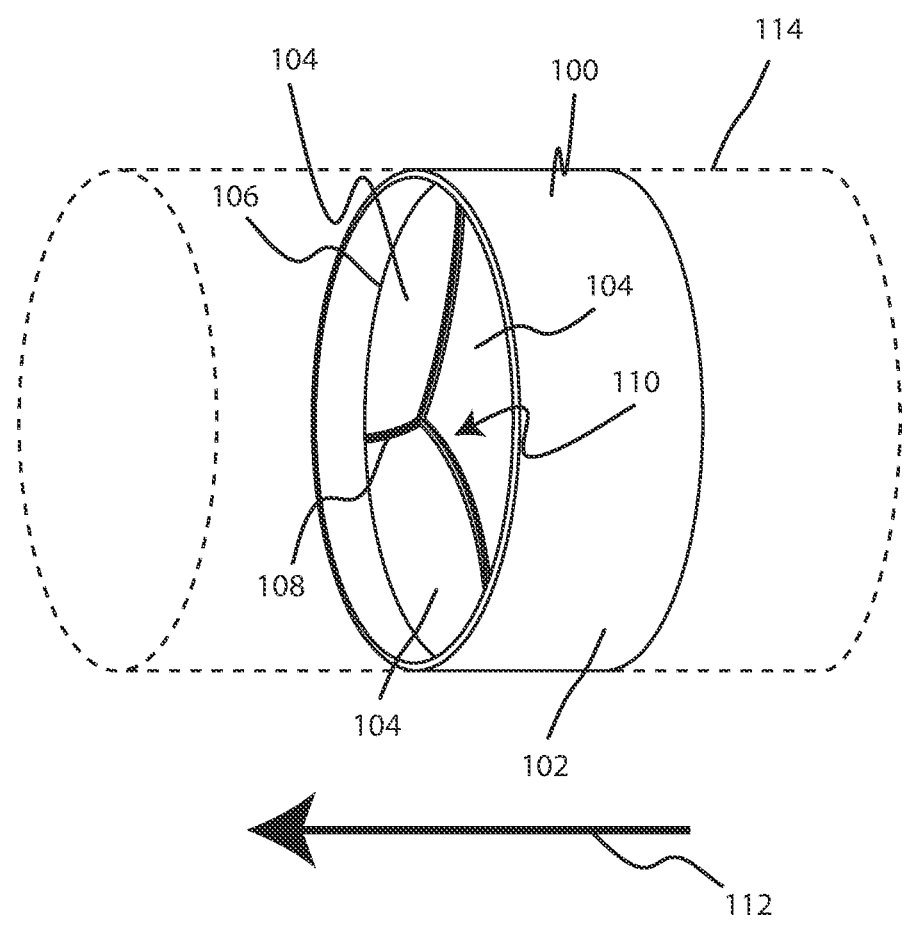
FIG. 1 is a schematic perspective view of a closed valve in a portion of an environment where it can be used, according to various embodiments.
Figure 2:
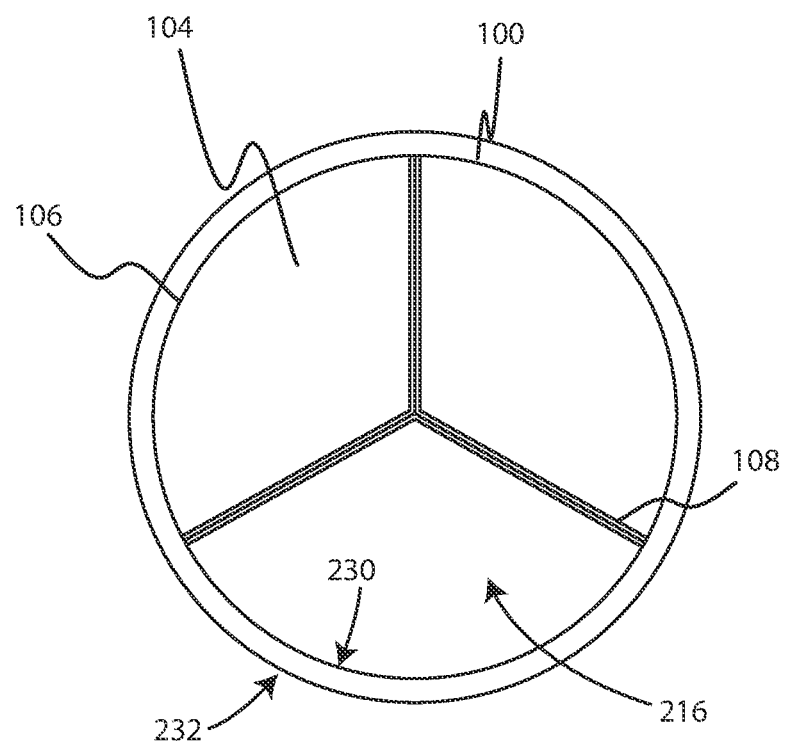
FIG. 2 is a schematic end view of a closed valve in a portion of an environment where it can be used, according to various embodiments.

The frame can include a plurality of struts. In various embodiments herein, the strut can define one or more radial bores or radial connection apertures. The connection apertures can be configured to receive a portion of a polymeric component thereby coupling the polymeric component to the frame. For example, a thermoplastic composition can infiltrate the connection aperture(s) and function to secure a polymeric component to the frame. In many cases, the thermoplastic composition that infiltrates the connection aperture(s) can also be used to form the polymeric component itself (e.g., the polymeric component secured to the frame). However, in other cases the thermoplastic composition that infiltrates the connection aperture may be a different material than that used to form the polymeric component secured to the frame. In some embodiments, a portion of the leaflet, inner skirt, or outer skirt can be polymeric and can extend through the strut, such as when the connection aperture(s) extends through the strut. In other embodiments, a portion of the leaflet, inner skirt, or outer skirt can terminate within the strut, such as when the connection aperture(s) does not extend completely through the strut. Some of the embodiments described herein can allow the valve to be at least partially assembled without the use of sutures or other secondary attachment means. FIG. 1 shows a schematic view of a closed valve 100 in a vessel 114, according to various embodiments. FIG. 2 shows an end view of the closed valve 100. It should be appreciated that the valve 100 can be any type of heart valve (e.g., a mitral valve, an aortic valve, etc.). In use, the valve 100 can be implanted (e.g., surgically or through transcatheter delivery) in a mammalian heart. The valve 100 can be configured to allow one-way flow through the valve 100, such as depicted by arrow 112. In an embodiment, the arrow 112 represents blood flow during systole.

The valve 100 can include a frame 102 defining a central lumen 216 (see FIG. 2) which, in some embodiments, can be substantially cylindrical. The side of the frame 102 and other components facing the central lumen 216 can be referred to as the luminal surface 230 or luminal side. The opposite side of the frame 102 and other components (e.g., facing away from the central lumen 216) can be referred to as the abluminal surface 232 or abluminal side. In various embodiments, the frame 102 can have a substantially circular cross-section. In other embodiments, the frame 102 can have a non-circular, such as a D-shaped, cross-section. In some embodiments, a non-circular frame 102 can be used to repair a mitral valve or another non-circular valve in the body. The frame 102, including at least some components thereof, can be formed of various materials including, but not limited to, metals and metal alloys, such as corrosion resistant metals and metal alloys, composites, ceramics, polymers, and the like. In some embodiments, the frame 102 can be at least partially formed of nitinol or NiTiCo.

The valve 100 can include a plurality of leaflets 104 disposed within the central lumen 216. Each leaflet 104 can include a respective root edge 106 coupled to the frame 102 and a respective free edge or coaptation edge 108 movable relative to the root edge 106 to coapt with the coaptation edges 108 of the other polymeric leaflets 104 along the coaptation region 110. In some embodiments, the plurality of leaflets 104 can be integrally formed with each other, such that the leaflets 104 are formed as a single unit. In some embodiments, a "root edge" can be a formed edge, such as when the leaflets 104 are formed in place on the frame 102. In some embodiments, the valve leaflets 104 can be formed integrally with other structures such as an integral skirt (inner and/or outer), base structures, liners, leaflets or the like and in those circumstances the "root edge" is not a cut or otherwise divided edge, but rather is the location opposite the coaptation edge where the valve leaflet integrally meets those other structures.

The coaptation edges 108 of the leaflets 104 move into coaptation with one another in a closed position (FIGS. 1 and 2) to substantially restrict fluid from flowing past the valve 100 in a direction opposite to arrow 112. Specifically, the leaflets 104 can coapt to fill up or close the central lumen of the valve 100 thereby impeding the flow of fluid opposite to arrow 112.

Figure 3:
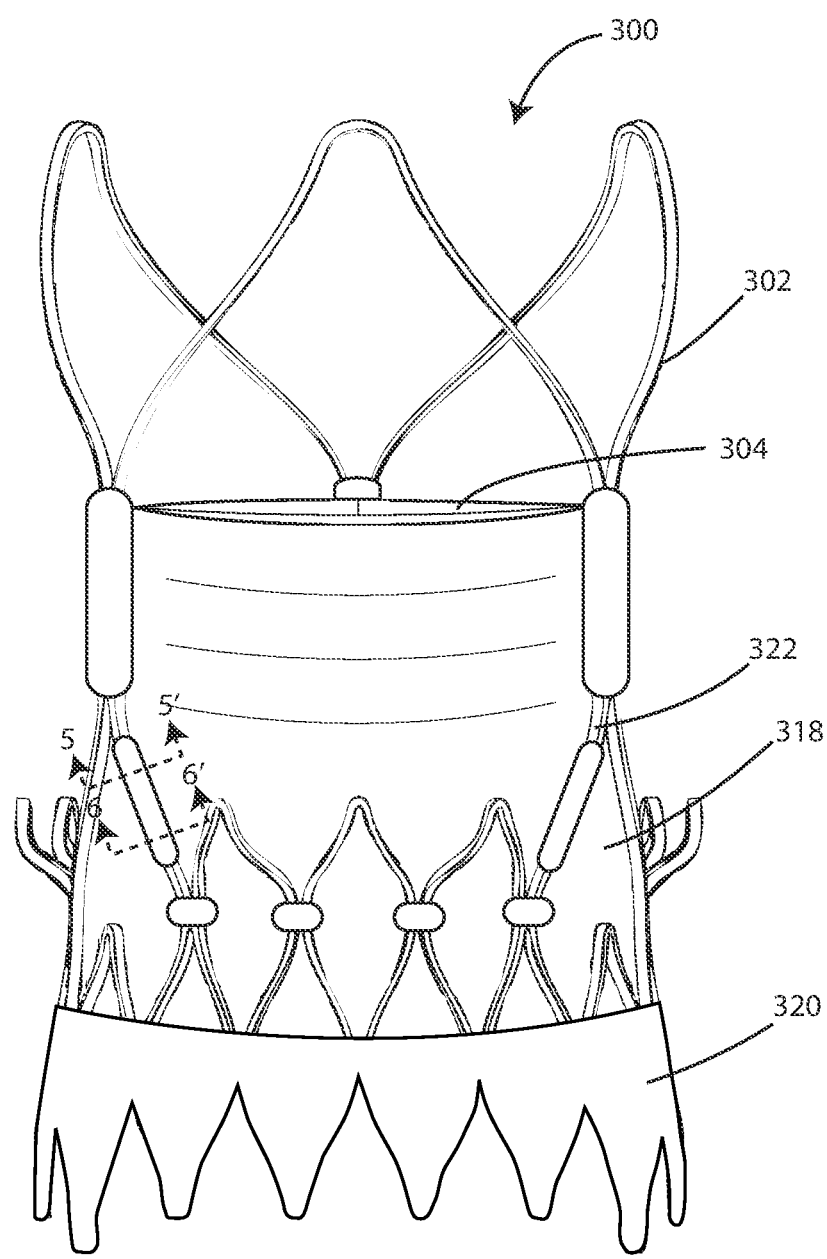
FIG. 3 is a schematic view of an implantable valve, according to various embodiments.

FIG. 3 shows a front view of an implantable valve 300, according to various embodiments. The valve 300 can include a frame 302, leaflets 304, an inner skirt 318, and an outer skirt 320. In some cases, the frame 302 can include a plurality of frame struts 322. However, frames lacking distinct struts are also contemplated herein.

The valve leaflets 304 can include a coaptation edge. The valve leaflets 304 can further include two connection portions. One connection portion can be disposed on either end of the coaptation edge such that the connection portions are contacting or adjacent to the frame. In some cases, the connections portions may also be referred to as commissural mounting tabs. In some embodiments, the connection portions can be disposed at least partially within a connection aperture 328 (see, e.g., FIG. 4) defined by a portion of the frame 302 thereby coupling or attaching the leaflet 304 to the frame 302. In some embodiments, the connection portions can be projections from the valve leaflet 304. The connection portions can be integral with the other portions of the valve leaflet 304, such that the leaflet 304 is a single part. In various embodiments, the connection portion of the valve leaflet 304 can extend completely through the connection apertures 328, such as when the connection apertures 328 extend completely through the struts 322 as shown in FIG. 5.

The total number of connection apertures can vary. In some embodiments, the frame of the valve can include at least 3, 6, 9, 12, 15, 18, 21, 30, 45, 60, 90, 120, 180, 360, 600 or 900 connection apertures, or can include a number of apertures falling within a range wherein any of the foregoing can serve as the upper or lower bound of the range.

Figure 6:
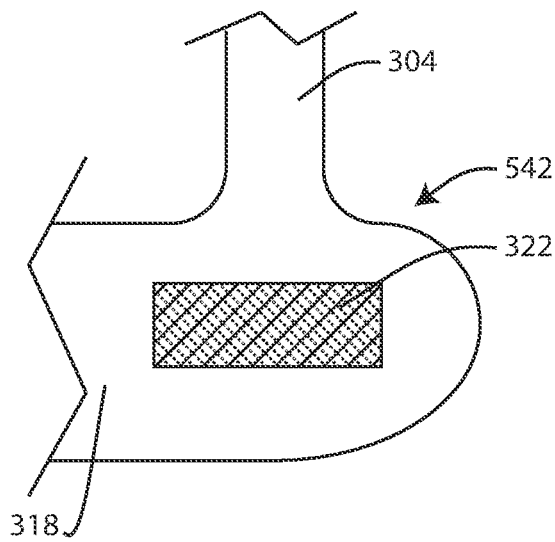
FIG. 6 is a schematic cross-section of a portion of the implantable valve as taken along line 6-6' of FIG. 3, according to various embodiments.

In some embodiments, the connection portions can encircle a portion of the strut 322, such as when the connection portion contacts a strut 322 at a location where the strut 322 does not define a connection aperture 328, such as shown in FIG. 6.

In various embodiments, the implantable valve 300 can include an inner skirt 318. The inner skirt 318 can define a substantially tubular shape. The inner skirt 318 can be disposed on a luminal surface of the frame 302. The luminal surface of the frame 302 can be a surface of the frame 302 that defines the central lumen 216. The inner skirt 318 can direct fluid, such as blood, flowing through the valve 300. The inner skirt 318 can ensure the fluid flows through the central lumen 216 of the valve 300 and does not flow around the leaflets 304 when they are in a closed configuration.

The inner skirt 318 can include a connection projection that extends from the inner skirt 318 and into a connection aperture 328. In some embodiments, a connection projection can extend around a portion of a strut 322. In additional embodiments, a connection projection can extend around a portion of a strut 322 and into a connection aperture 328. The connection projections can interact with the frame 302 to attach or couple the inner skirt 318 to the frame through surface area contact and/or a form fitting configuration.

In various embodiments, the implantable valve 300 can include an outer skirt 320. The outer skirt 320 can define a substantially tubular shape. The outer skirt 320 can be disposed on an abluminal surface of the frame 302. The abluminal surface of the frame 302 can be a surface of the frame 302 that is external to the central lumen 216. The outer skirt 320 can be disposed between the frame 302 and the vessel wall in order to prevent fluid, such as blood, flowing around the valve 300. The outer skirt 320 can ensure the fluid flows through the valve 300 and does not flow around the valve 300, such as to ensure that the leaflets 304 can stop the flow of fluid when in a closed position.

The outer skirt 320 can include a connection projection that extends from the outer skirt 320 and into a connection aperture 328. In some embodiments, a connection projection can extend around a portion of a strut 322. In additional embodiments, a connection projection can extend around a portion of a strut 322 and into a connection aperture 328. The connection projections can interact with the frame 302 to attach or couple the outer skirt 320 to the frame 302, such as through surface area contact or a form fitting configuration.

In some embodiments, the leaflet 304 can be comprised of a polymer, such as a thermoplastic polymer. In some embodiments, the leaflet 304 can include at least 50 percent by weight of a polymer. In some embodiments, the inner skirt 318 can include a polymer, such as a thermoplastic polymer. In some embodiments, the inner skirt 318 can include at least 50 percent by weight of a polymer. In some embodiments, the outer skirt 320 can include a polymer, such as a thermoplastic polymer. In some embodiments, the outer skirt 320 can include at least 50 percent by weight of a polymer. In some embodiments one or more of the leaflet 304, the inner skirt 318, and the outer skirt 320 can be formed of the same polymer or polymers. In some embodiments, the polymer can be a polyurethane. However, further details of exemplary polymers are described in greater detail below.

Figure 4:
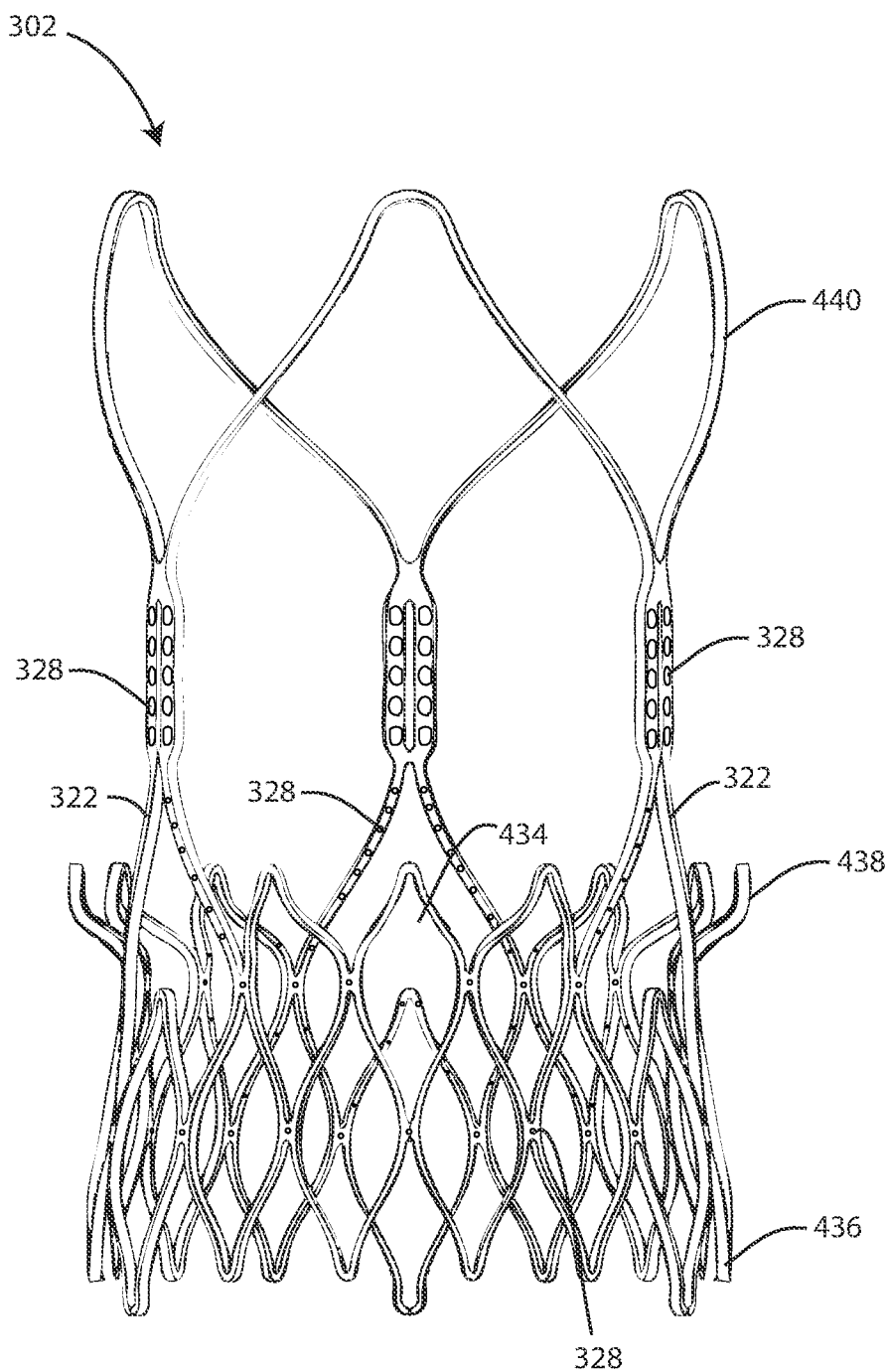
FIG. 4 is a schematic view of a frame, according to various embodiments.
Figure 5:
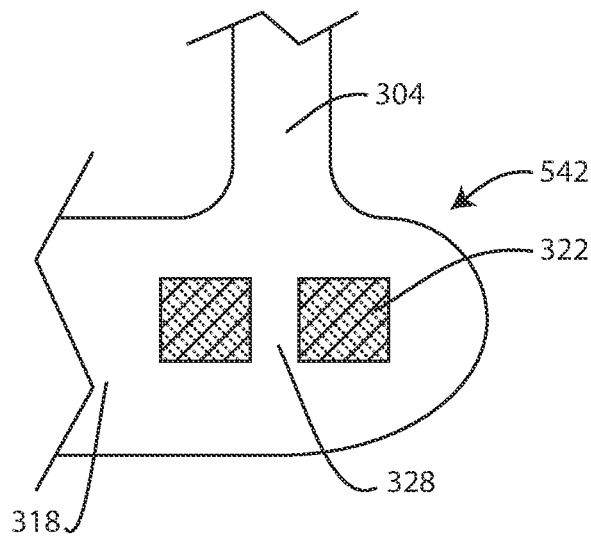
FIG. 5 is a schematic cross-section of a portion of the implantable valve as taken along line 5-5' of FIG. 3, according to various embodiments.

FIG. 4 shows a schematic view of a frame 302, according to various embodiments. The frame can include the plurality of frame struts 322. The frame struts 322 can be rods, bars, plates, or other projections that define a framework or lattice structure. In some embodiments, the frame can define open spaces 434 between the frame struts 322. However, in other embodiments the frame may not include such open spaces 434.

In some embodiments, the frame struts 322 can define a lower crown 436, an upper crown 438 and a plurality of stabilization arches 440. In some embodiments, the inner skirt 318 can be coupled to the lower crown 436 and/or the upper crown 438. In other embodiments, the inner skirt 318 is only coupled to the upper crown 438. In some embodiments, the outer skirt 320 can be coupled to the lower crown 436 and/or the upper crown 438. In other embodiments, the outer skirt 320 is only coupled to the lower crown 436. In some embodiments, the valve leaflets 304 can be coupled to the frame at a position that is at or just below the stabilization arches 440 and above the upper crown 438.

In various embodiments, at least one of the frame struts 322 can define a connection aperture 328. A connection aperture 328 can be configured to receive a connection portion or a projection from a valve leaflet 304, an inner skirt 318, or an outer skirt 320 to aid in coupling the valve leaflet 304, the inner skirt 318, or the outer skirt 320 to the frame 302. In some embodiments, the connection aperture 328 can be defined radially around the frame 302. In some embodiments, the connection aperture 328 can be a bore.

In various embodiments, a strut 322 can define a plurality of connection apertures 328. In some embodiments, the density of connection apertures 328 can vary along the length of a strut 322, such that the frequency of the connection apertures 328 can change along the strut 322. References to connection aperture density herein shall refer to the number of connection apertures per unit length of the component into which they are disposed, such as a strut. In some embodiments, the density of connection apertures 328 is the highest at a portion of the frame 302 which is subjected to the highest stresses. In some embodiments, the density of connection apertures 328 is the highest at a portion of the frame 302 where the attached polymeric component (e.g., the leaflets, the inner skirt, and/or the outer skirt) is subjected to the highest load concentration adjacent to the frame 302. The additional connection apertures 328 can allow for an increased amount of surface area of the frame 302 being in contact with the polymeric component, such as to provide a more secure coupling between the frame 302 and the polymeric component. In some embodiments, a location that is at or just below the stabilization arches 440 and above the upper crown 438 are subjected to the highest stresses, and can include a greater density of connection apertures 328 as compared to other places on the frame 302. In many embodiments, the frame connections with the valve leaflets 304 are under greater stress than the connections with the inner skirt 318 or the outer skirt 320, thus the frame portions that connect to the valve leaflets 304 may have a higher density of apertures as compared to the frame portions with connections to the inner skirt 318 or the outer skirt 320.

A schematic cross-section (as taken along line 5-5' of FIG. 3) of a connection between a valve leaflet 304 and a frame strut 322 is shown in FIG. 5. This cross-section was chosen to illustrate the view passing through a strut with a connection aperture therein. In various embodiments, the connection portion 542 can extend into and through the connection aperture 328. In various embodiments, the connection portion 542 can extend around a portion of the frame strut 322, such as to encircle or surround a portion of the frame strut 322 as shown in FIG. 5. In some embodiments, the section of the connection portion 542 that extends through the connection aperture 328 can connect with or be coupled to the section of the connection portion 542 that extends around the frame strut 322.

In some embodiments, a connection portion 542 of the valve leaflet 304, the inner skirt 318, or the outer skirt 320 can contact and connect with the frame 302 along a portion of a frame strut 322 that does not define a connection aperture. FIG. 6 shows a cross-section (as taken along line 6-6' of FIG. 3) of a connection portion 542 of a valve leaflet 304 connecting with the frame 302 by encircling a portion of the frame strut 322. This cross-section was chosen to illustrate a view passing through a strut without a connection aperture. In other embodiments, the connection portion 542 can extend around only a portion of the frame strut 322, such as to not completely encircle or surround the frame strut 322.

As discussed above, the frame struts 322 can define one or more connection apertures 328. In some embodiments, the connection aperture 328 can extend outward from an inner surface 744 of the strut 322 that defines the luminal surface of the frame 302. In other embodiments, the connection aperture 328 can extend inward from an outer surface 746 of the frame strut 322, such as the surface of the frame strut 322 that defines a portion of the abluminal surface. In some embodiments, the outer skirt 320 can be connected to the frame 302 via a connection aperture 328 that extends inward from the outer surface 746 of the frame strut 322.

Figure 7:
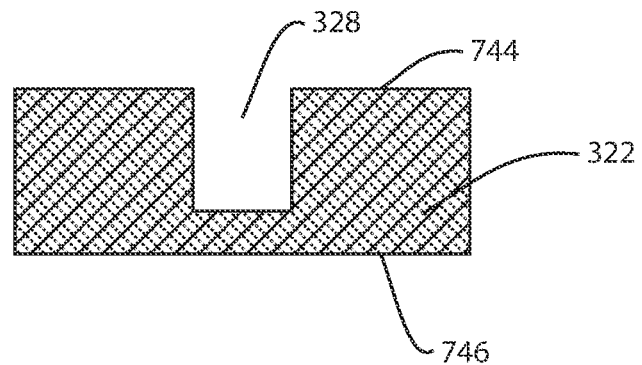
FIG. 7 is a schematic cross-section of a portion of the frame, according to various embodiments.
Figure 8:
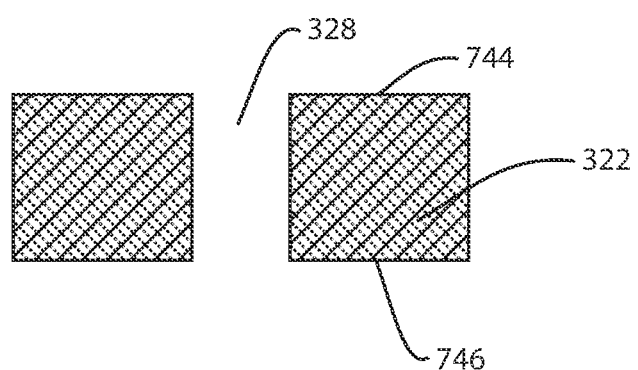
FIG. 8 is a schematic cross-section of a portion of the frame, according to various embodiments.

FIG. 7 shows a schematic cross-section of a portion of a frame strut 322 with the connection aperture 328 not extending completely through. In some embodiments, the connection aperture only extends 20% of the way through the frame strut 322, such as 20% of the distance from the inner surface 744 to the outer surface 746. In other embodiments, the connection aperture 328 can extend at least 30%, at least 40%, at least 50%, at least 60%, at least 70%, at least 80%, or at least 90% of the way through the frame strut 322. In some embodiments, the connection aperture 328 can be a through hole or extend completely through the frame strut 322, such as shown in FIG. 8.

Figure 9:
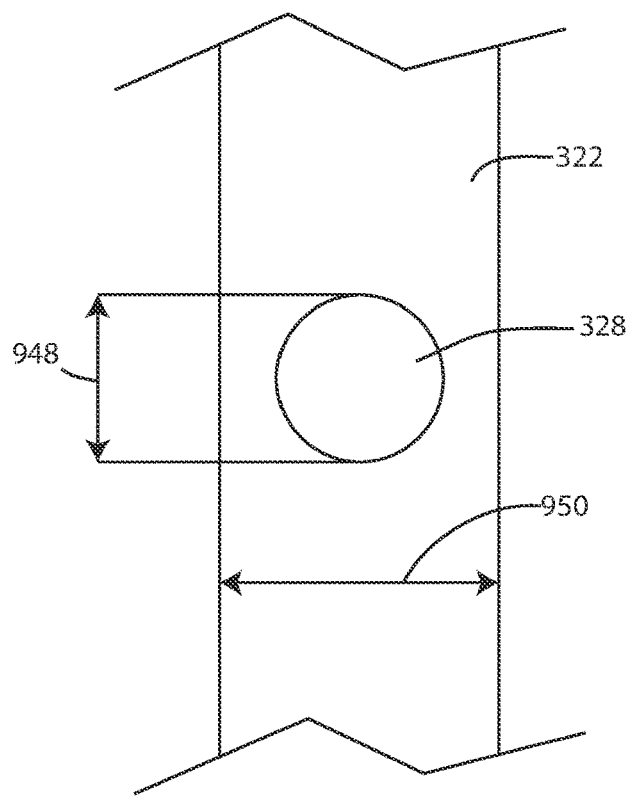
FIG. 9 is a schematic view of a portion of the frame, according to various embodiments.

FIG. 9 shows a portion of the frame strut with a connection aperture 328. In some embodiments, the connection aperture 328 can be cylindrical and have a circular cross-section, such as shown in FIG. 9. In various embodiments, the connection aperture 328 can have a diameter 948 of at least 0.05 mm and not more than 0.5 mm. In various embodiments, the connection aperture 328 can have a diameter 948 of at least 0.1 mm and not more than 0.4 mm. In various embodiments, the connection aperture 328 can have a diameter 948 of at least 0.2 mm and not more than 0.3 mm.

In some embodiments, the connection aperture 328 can have a cross-sectional area of at least 0.002 $mm^2$ and not more than 0.2 $mm^2$. In some embodiments, the connection aperture 328 can have a cross-sectional area of at least 0.007 $mm^2$ and not more than 0.13 $mm^2$. In some embodiments, the connection aperture 328 can have a cross-sectional area of at least 0.03 $mm^2$ and not more than 0.07 $mm^2$.

The frame strut 322 can have a width 950. In some embodiments, the diameter 948 can be greater than or equal to 10% of the width 950. In some embodiments, the diameter 948 can be greater than or equal to 15% of the width 950.

In some embodiments, the diameter 948 can be greater than or equal to 20% of the width 950. In some embodiments, the diameter 948 can be greater than or equal to 25% of the width 950. In some embodiments, the diameter 948 can be greater than or equal to 30% of the width 950.

It should be understood that the diameter 948 can also be expressed as being within a range, such as being greater than the values above and being less than the values listed below. In some embodiments, the diameter 948 can be less than or equal to 90% of the width 950. In some embodiments, the diameter 948 can be less than or equal to 85% of the width 950. In some embodiments, the diameter 948 can be less than or equal to 80% of the width 950. In some embodiments, the diameter 948 can be less than or equal to 75% of the width 950. In some embodiments, the diameter 948 can be less than or equal to 70% of the width 950.

Figure 10:
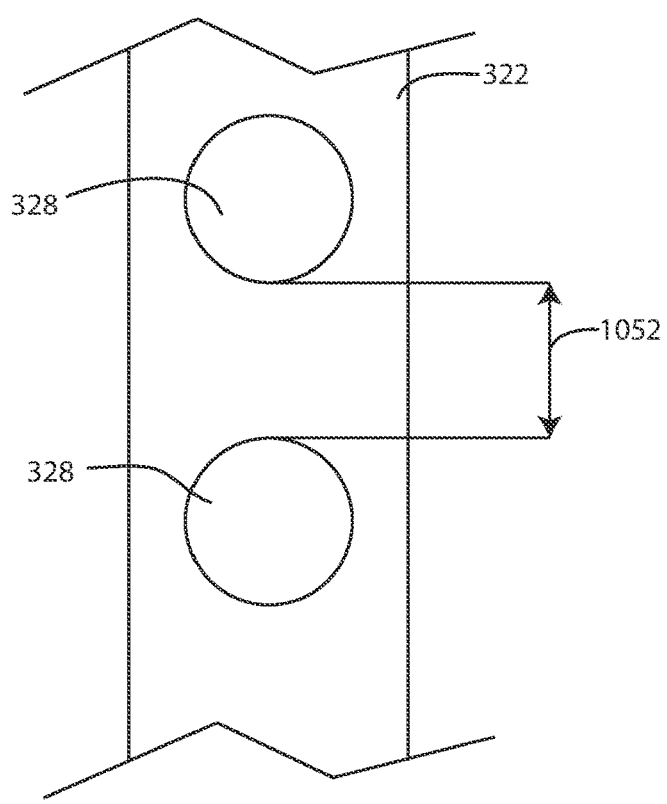
FIG. 10 is a schematic view of a portion of the frame, according to various embodiments.

FIG. 10 shows a front view of a portion of a frame strut 322 with two connection apertures 328. As mentioned above, the density of connection apertures 328 or distance 1052 between connection apertures 328 can vary along a frame strut 322. In some embodiments, the distance 1052 between two adjacent connection apertures 328 can be at least 0.3 mm and not more than 3.0 mm. In some embodiments, the distance 1052 between two adjacent connection apertures 328 can be at least 0.4 mm and not more than 2.5 mm. In some embodiments, the distance 1052 between two adjacent connection apertures 328 can be at least 0.5 mm and not more than 2.0 mm. In some embodiments, the distance 1052 between two adjacent connection apertures 328 can be at least 0.6 mm and not more than 1.9 mm. In some embodiments, the distance 1052 between two adjacent connection apertures 328 can be at least 0.7 mm and not more than 1.8 mm.

Figure 11:
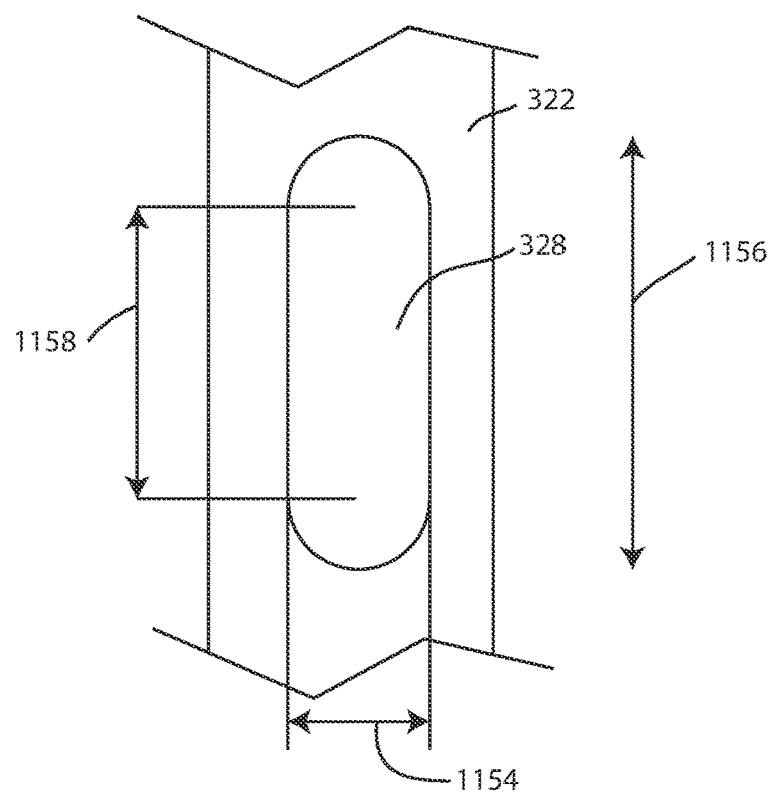
FIG. 11 is a schematic view of a portion of the frame, according to various embodiments.

FIG. 11 shows a portion of a frame strut 322 with a connection aperture 328. In some embodiments, the connection aperture 328 can be an elongated slot. The connection aperture 328 can have a width 1154 which can be equivalent to the diameter 948 shown in FIG. 9. The connection aperture 328 can also have a length 1156. In some embodiments, the ratio of the length 1156 to the width 1154 can be 5:1 or less, 4:1 or less, 3:1 or less, or 2:1 or less.

The connection aperture 328 can include two arcs or curves with the centers separated by a distance 1158. In some embodiments, the distance 1158 between the centers can be a ratio relative to the diameter 948 or width 1154. In some embodiments, the distance 1158 can be greater than or equal to 50% of the diameter 948 or width 1154. The distance 1158 can also be equal to or less than 2 times the diameter 948 or width 1154.

Figure 12:
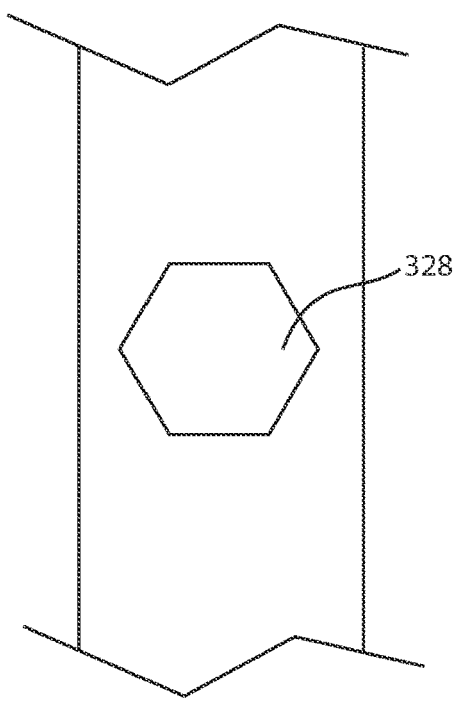
FIG. 12 is a schematic view of a portion of the frame, according to various embodiments.

In some embodiments, the connection aperture 328 can include a circular cross-section, such as shown in FIG. 9. In other embodiments, the connection aperture 328 can include an elongated slot cross-section, such as shown in FIG. 11. In other embodiments, the connection aperture 328 can include a cross-section with linear components such as a triangle, square, pentagon, or hexagon (shown in FIG. 12).

Polymers

Many different polymers can be used to form components herein such as the leaflets, inner skirt, outer skirt and the like. In some embodiments, exemplary polymers are synthetic polymers. However, in some embodiments, non-synthetic polymers can also be used. In some embodiments, the polymer can start as a flowable and/or moldable composition. As a flowable or moldable composition, the polymer composition can enter connection apertures described herein. In some cases, pressure can be applied to aid in causing the polymer composition to enter connection apertures. In some embodiments, a state of flowability can be achieved through heating the polymer to a temperature above its melting temperature. After the polymeric composition has entered connection apertures, it can be allowed to cool to form a strong point of connection with the frame or other component bearing a connection aperture. In some examples, the polymer can be a thermoplastic polymer. Thermoplastic polymers are those that melt and flow. In some embodiments, a state of flowability can be present prior to a possible later step of crosslinking, curing, solvent evaporation and/or polymerization. Thus, in some examples, the polymer can be a thermoset polymer in a final form. Thermoset polymers are those that do not melt and flow, typically because of crosslinking.

In some embodiments, polymers herein can include one or more polymers selected from the group consisting of poly(ethylene oxide), polyethylene, polyesters, polyisobutylene polyurethane (PIBU), poly(styrene-block-isobutylene-block-styrene (SIBS), polypropylene, polystyrene, polyvinylchloride, polyisobutylene (PIB), poly(styrene) polyurethanes, polyvinylidene difluoride, poly(methyl methacrylate), polyethylene glycol, polyanilines, polypyrroles, polythiophenes, polyphenols, polyacetylenes, polyphenylenes, polyacrylonitriles, polylactic acids, polycaprolactone, polyglycolides, polyvinyl acetates, polyethylene terephthalate (PET), cellulose acetate, chitosan, proteins, carbohydrates and copolymers including one or more of these. In some embodiments, different portions of the valve can be formed of different polymers or polymer alloys, but in other embodiments the same polymer or polymer alloy can be used.

The embodiments of the present technology described herein are not intended to be exhaustive or to limit the technology to the precise forms disclosed in the following detailed description. Rather, the embodiments are chosen and described so that others skilled in the art can appreciate and understand the principles and practices of the present technology.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

As used herein, the phrase "is comprised of" with reference to a component and a material shall mean that the reference component includes that material, but is not limited to only including that material. As such, a valve leaflet that is comprised of a thermoplastic polymer is a valve leaflet that includes at least some percentage by weight of a thermoplastic polymer, but can also include other materials such as other polymers, metals, composites, glasses, tissues, reinforcing fibers, inserts, and the like.

As used herein, the phrase "formed of" with reference to a component and a material shall mean that the reference component includes that material, but is not limited to only including that material. As such, a valve leaflet that is formed of a thermoplastic polymer is a valve leaflet that includes at least some percentage by weight of a thermoplastic polymer, but can also include other materials such as other polymers, metals, composites, glasses, tissues, reinforcing fibers, inserts, and the like.

All publications and patent applications in this specification are indicative of the level of ordinary skill in the art to which this technology pertains. All publications and patent applications are herein incorporated by reference to the same extent as if each individual publication or patent application was specifically and individually indicated by reference.

The technology has been described with reference to various specific and preferred embodiments and techniques. However, it should be understood that many variations and modifications may be made while remaining within the spirit and scope of the technology.

The invention claimed is:

1. An implantable valve, comprising:
a frame comprising a plurality of frame struts, wherein the frame defines a central lumen and at least one of the frame struts defines a connection aperture;
at least one valve leaflet comprising:
a coaptation edge;
two connection portions, one connection portion disposed on either end of the coaptation edge;
wherein the connection portion is disposed within the connection aperture thereby coupling the valve leaflet to the frame;
wherein the coaptation edge and the two connection portions are integrally formed components of the at least one valve leaflet;
wherein some portions of the frame are not encircled by connection portions with the at least one valve leaflet coupled to the frame.

2. The implantable valve of claim 1, wherein the connection aperture extends at least 80 percent through the strut.

3. The implantable valve of claim 1, wherein the connection aperture extends completely through the strut.

4. The implantable valve of claim 3, wherein at least one of the connection portions of the valve leaflet extends through the connection aperture.

5. The implantable valve of claim 1, further comprising a plurality of struts, each of the struts defining a plurality of connection apertures.

6. The implantable valve of claim 5, wherein the plurality of frame struts define a lower crown, an upper crown and a plurality of stabilization arches.

7. The implantable valve of claim 1, wherein the at least one leaflet is comprised of a thermoplastic polymer.

8. The implantable valve of claim 1, wherein the connection aperture has a diameter of at least 0.1 mm and not more than 0.4 mm.

9. The implantable valve of claim 1, further comprising:
an inner skirt, wherein the inner skirt is disposed on a luminal surface of the frame; the inner skirt comprising a skirt connection projection that extends into a skirt connection aperture defined by a strut thereby coupling the inner skirt to the frame.

10. The implantable valve of claim 9, wherein the inner skirt is integrally formed with the at least one valve leaflet.

11. The implantable valve of claim 9, wherein the inner skirt is integrally formed with the skirt connection projection.

12. The implantable valve of claim 1, further comprising:
an outer skirt, wherein the outer skirt is disposed on an abluminal surface of the frame, the outer skirt comprising a skirt connection projection that extends into a skirt connection aperture defined by a strut thereby coupling the outer skirt to the frame.

13. An implantable valve, comprising:
a frame comprising a plurality of frame struts, wherein the frame defines a central lumen and at least one of the frame struts defines a connection aperture;
an inner skirt, wherein the inner skirt is disposed on a luminal surface of the frame; the inner skirt comprising a skirt connection projection that extends into a skirt connection aperture defined by a strut thereby coupling the inner skirt to the frame; and
at least one valve leaflet comprising:
a coaptation edge;
two valve connection portions, one valve connection portion disposed on either end of the coaptation edge;
wherein the valve connection portion is disposed within the connection aperture thereby coupling the valve leaflet to the frame;
wherein the inner skirt and the skirt connection projection are integrally formed with each other;
wherein some portions of the frame are not encircled by connection portions with the inner skirt coupled to the frame.

14. The implantable valve of claim 13, wherein the at least one leaflet and the inner skirt are comprised of a thermoplastic polymer.

15. The implantable valve of claim 13, wherein the connection aperture has a diameter of at least 0.1 mm and not more than 0.4 mm.

16. The implantable valve of claim 13, further comprising: an outer skirt, wherein the outer skirt is disposed on an abluminal surface of the frame.

17. An implantable valve, comprising:
a frame comprising a plurality of frame struts, wherein the frame defines a central lumen and at least one of the frame struts defines a connection aperture;
an outer skirt, wherein the outer skirt is disposed on an abluminal surface of the frame; the outer skirt comprising a skirt connection projection that extends into a skirt connection aperture defined by a strut thereby coupling the outer skirt to the frame; and
at least one valve leaflet comprising:
a coaptation edge;
two valve connection portions, one valve connection portion disposed on either end of the coaptation edge;
wherein the valve connection portion is disposed within the connection aperture thereby coupling the valve leaflet to the frame;
wherein the outer skirt and the skirt connection projection are integrally formed with each other,
wherein some portions of the frame are not encircled by connection portions with the outer skirt coupled to the frame.

18. The implantable valve of claim 17, wherein the at least one leaflet and the outer skirt are comprised of a thermoplastic polymer.

19. The implantable valve of claim 17, wherein the connection aperture has a diameter of at least 0.1 mm and not more than 0.4 mm.

20. The implantable valve of claim 17, further comprising: an inner skirt, wherein the inner skirt is disposed on a luminal surface of the frame.

* * * * *